US00PP25635P3

(12) United States Plant Patent
Eugenin

(10) Patent No.: US PP25,635 P3
(45) Date of Patent: Jun. 23, 2015

(54) AVOCADO TREE NAMED 'EUGENIN'

(50) Latin Name: ***Persea americana* Mill.**
Varietal Denomination: Eugenin

(75) Inventor: Javier Eugenin, Hijuelas (CL)

(73) Assignee: Corretajes Percit LTDA., Quillota (CL)

( * ) Notice: Subject to any disclaimer, the term of this patent is extended or adjusted under 35 U.S.C. 154(b) by 33 days.

(21) Appl. No.: 13/507,592

(22) Filed: Jul. 12, 2012

(65) Prior Publication Data

US 2014/0020142 P1 Jan. 16, 2014

(51) Int. Cl.
*A01H 5/00* (2006.01)

(52) U.S. Cl.
USPC ..... Plt./200

(58) Field of Classification Search
USPC ..... Plt./200
See application file for complete search history.

(56) References Cited

U.S. PATENT DOCUMENTS

PP139 P * 8/1935 Hass ..... Plt./200
PP9,530 P * 4/1996 Salas ..... Plt./200
PP11,173 P * 1/2000 Vega ..... Plt./200
PP17,947 P3 * 8/2007 Darvas ..... Plt./200
PP23,885 P3 * 9/2013 Pflum ..... Plt./200
PP24,279 P3 * 3/2014 Menge et al. ..... Plt./200

OTHER PUBLICATIONS

UPOV PLUTO Citation for 'Eugenin' 2007.*
Arpaia, M. "Enhancement of Avocado Productivity" 2008 Production Research Report California Avocado Commission 2008.*
Chen, H. et al. "Tracing the Geographic Origins of Major Avocado Cultivars." Journal of Heredity 2009:100(1) 56-65 Sep. 8, 2008.*
Gardiazabal, F. et al. "Evaluaction De Dos Nuevas Variedades De Paltos (*Persea americana* Mill.) Similares Al. Cv. Hass Obtenidas en Chile" Proceedings VI World Avocado Congress 2007 Nov. ISBN 978-956-17-0413-8.*
Alcaraz, M. et al. Moleculart Chareacterization and Genetic Diversity in an avocado collectiono of cultivars and local Spanish genotypes using SSRs Hereditase 144: 244-253 (2007).*
Francisco Gardiazabal I. et al.; Evaluation of Two New Hass Type Varieties Found in Chile; 11 pages; 2007.
Michael T. Clegg et al.; Assessing the Genetic Determination of Valuable Avocado Traits . . . ; 2007 Production Research Report, California Avocado Commission; 5 pages.

* cited by examiner

*Primary Examiner* — Kent L Bell
(74) *Attorney, Agent, or Firm* — Kelly & Kelley, LLP

(57) ABSTRACT

The 'Eugenin' avocado variety is notable for its larger fruit size and seed size, than that of the 'Hass' variety.

7 Drawing Sheets

Latin name of the genus and species: *Persea americana* Mill.

Varietal denomination: 'Eugenin'.

BACKGROUND OF THE INVENTION

Currently, the main avocado variety grown in the word is 'Hass' (U.S. Plant Pat. No. 139, the contents of which are incorporated herein by reference). The main markets have year-round supply of 'Hass' avocados and end consumers are very used to buying 'Hass'. Many other avocado varieties have been created and patented in the last twenty years, but none of them has been able to obtain important interest from growers. The main reason for the lack of interest is that the market still prefers 'Hass'.

Avocado fruit size is one of the major issues that growers of most production areas face when growing 'Hass' avocados. The grower's net return can be doubled when prices from small fruit and big fruit (+200 grams) are compared. There are varieties, such as Esther (U.S. Plant Pat. No. 5,309), that solve the fruit size problem. However, the skin of the fruit is green and the market has no major interest in it.

SUMMARY OF THE INVENTION

'Eugenin' is a new and distinct variety of avocado tree *Persea americana* Mill. The 'Eugenin' variety was first discovered in 1997 by Mr. Javier Eugenin, who noted a tree in his cultivated avocado orchard located in Hijuelas, in the Aconcagua Valley in Chile. The tree was discovered after observing through several years that its fruit size was consistently higher than the 'Hass' trees from the orchard. After several evaluations, it was determined that the 'Eugenin' tree consistently produced larger fruit than 'Hass' trees.

The 'Eugenin' discovered tree is presumed to be a mutated bud (it is a whole tree mutation) from a spontaneous mutation of 'Hass'. Budwood from the originally discovered 'Eugenin' mother tree was grafted into new trees, which were planted in January 2000, as a non-propagation trial in Nogales, Chile. It has since been observed to remain true to type and the material and mutation is stable. The tree was discovered, after observing through several years, that the fruit size was consistently larger than corresponding 'Hass' trees.

BRIEF DESCRIPTION OF THE PHOTOGRAPHS

The accompanying photographs show specimens of the tree and plant parts of the new 'Eugenin' variety.

DETAILED BOTANICAL DESCRIPTION OF THE VARIETY

The following is a detailed botanical description of the 'Eugenin' variety, sometimes referred to by the code names Andes 4 or GAMA 4021 by the breeder.

The following detailed botanical description is based on observations of trees which were grafted budwood from the 'Eugenin' mother tree (FIG. 1) and planted in the year 2000, as a non-propagation trial in Nogales, Chile. A multi-year study of these trees planted in 2000, ensured that the plant material and mutation is stable. The 'Eugenin' variety is nearly identical to 'Hass', except that it has a slight early flowering as compared to 'Hass' and produces larger fruit than 'Hass'. Otherwise, it is nearly identical in color and appearance as to 'Hass' trees.

Figure 1:
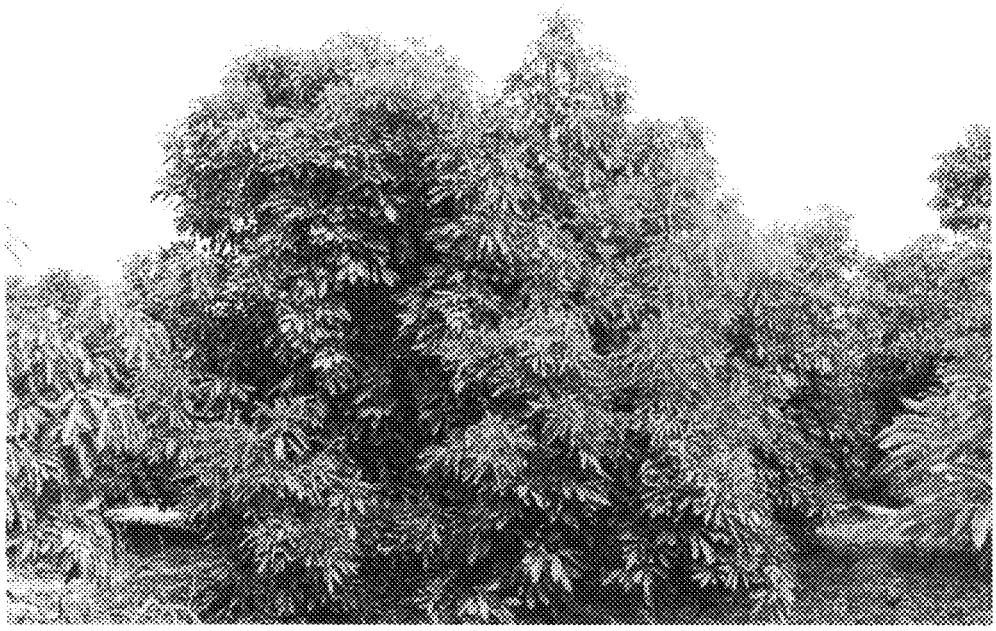
FIG. 1 is a photograph of the originally discovered 'Eugenin' mother tree.
Figure 2:
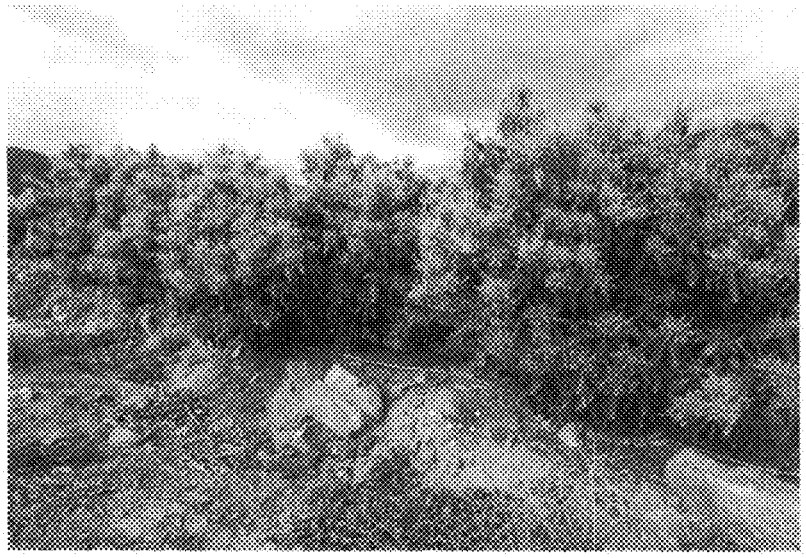
FIG. 2 is a photograph depicting 'Eugenin' trees flowering.
Figure 6:
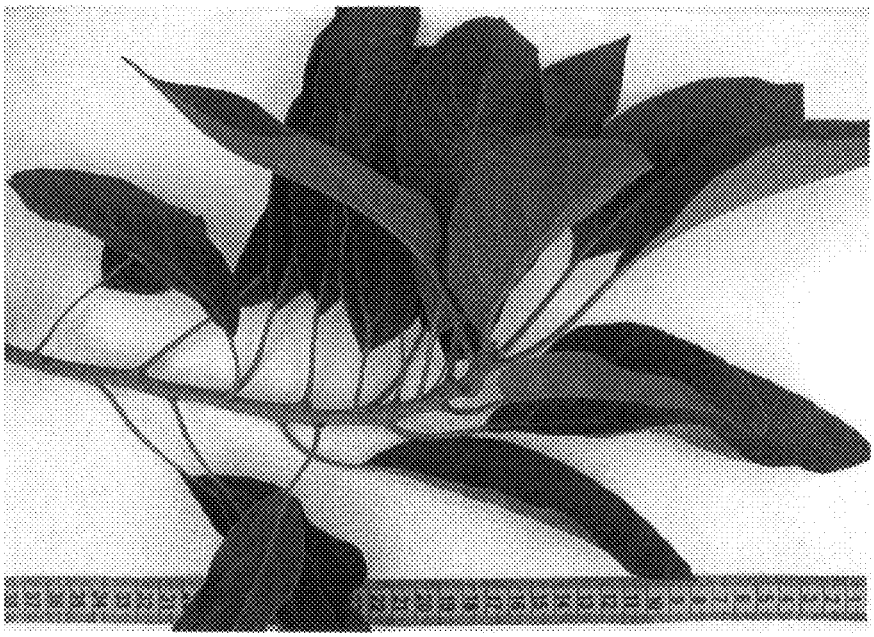
FIG. 6 is a photograph illustrating mature spring shoot.
Figure 7:
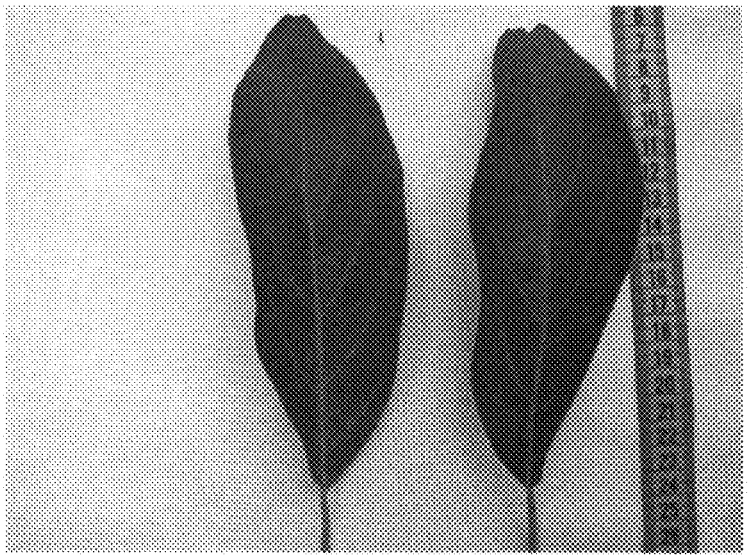
FIG. 7 is a photograph depicting mature spring leafs.

The 'Eugenin' tree presents a spreading growth habit, as illustrated in FIGS. 1 and 2. The young shoots are reddish in color. The anise aroma of the leaf blade is weak or absent. The inflorescence flowering type is similar to 'Hass' Type A. As illustrated in FIGS. 6 and 7, the mature leaf has a color, glossiness, and prominence of veins similar to 'Hass'.

Figure 3:
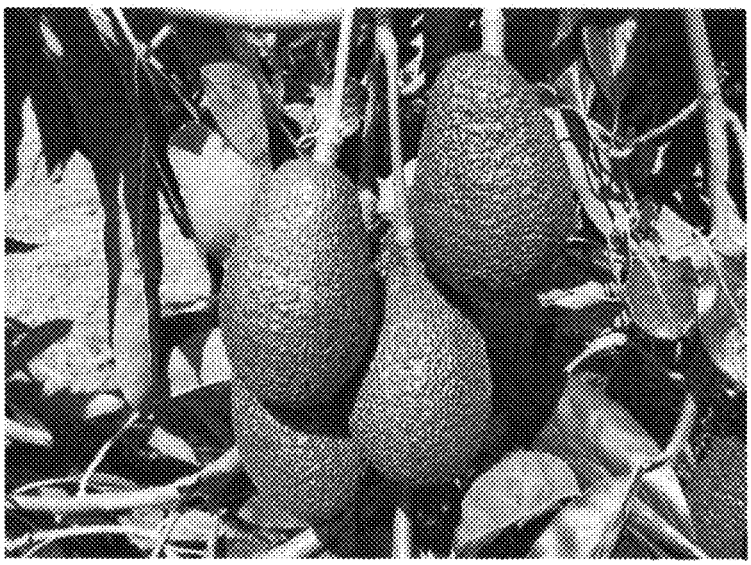
FIG. 3 is a photograph depicting fruit and leaves of 'Eugenin'.
Figure 4:
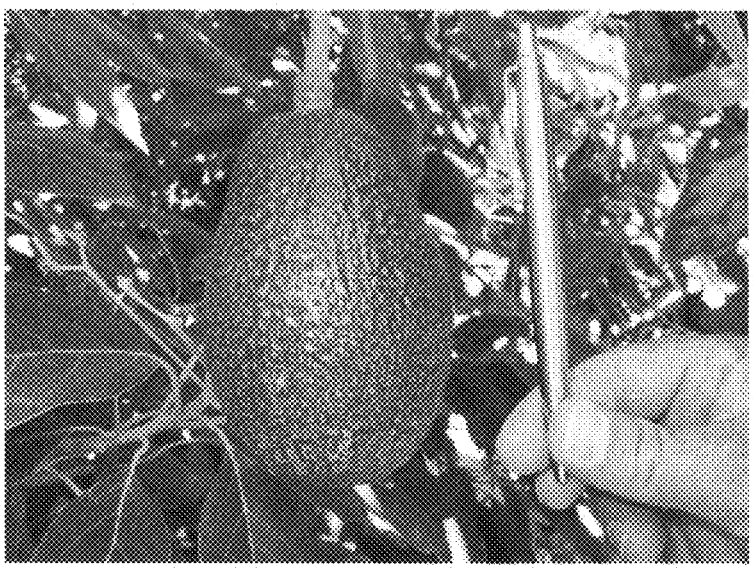
FIG. 4 is a photograph depicting fruit and leaves next to a hand holding a pen for size reference.
Figure 5:
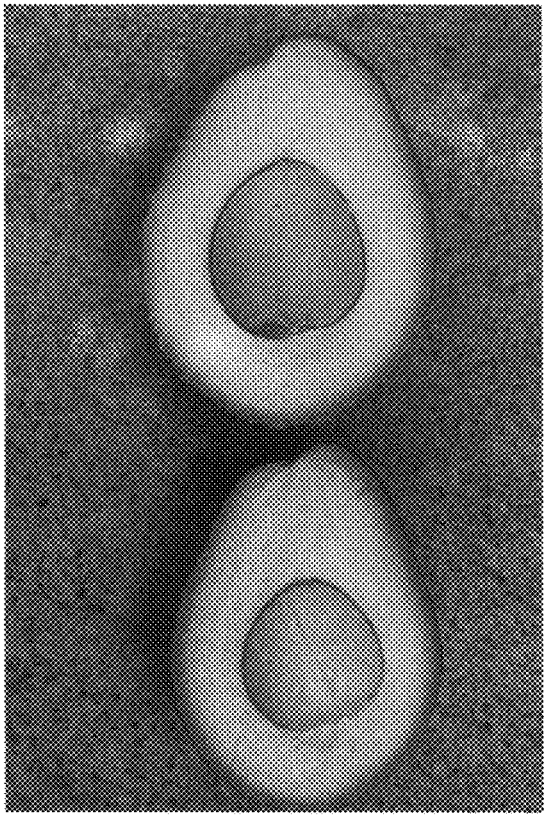
FIG. 5 is a photograph depicting sectioned fruit of the 'Eugenin' above 'Hass' fruit, illustrating that the fruit and seed is larger in 'Eugenin' than that of 'Hass'.

With respect to the fruit, as shown in FIGS. 3 and 4, the surface of the mature fruit is rough, similar to 'Hass'. The thickness of the pedicel compared to the peduncle, at the junction, is thicker. The pedicel length is long, similar to 'Hass'. However, the pedicel shape is cylindrical, and does not include a "nail head". The ripe fruit color is dark purple or black, similar to 'Hass'. The thickness of the ripe fruit skin is moderately thick, as 'Hass'. As illustrated in FIG. 5, the fruit is larger than that of 'Hass'. Moreover, the polar and equatorial diameter of the 'Eugenin' fruit is greater than 'Hass', resulting in larger fruit and higher average weight. Furthermore, the polar diameter/equatorial diameter ratio is greater, so that the 'Eugenin' fruit is more elongated than 'Hass'. The shape of the seed and longitudinal section is ovate. The seed size is generally larger, as illustrated in FIG. 5.

The 'Eugenin' variety has a slight early flowering as compared to 'Hass'. The 'Eugenin' variety flowering tends to be higher than 'Hass', and reaches a peak approximately a week before 'Hass'. The end of the flowering period for 'Eugenin' is approximately a week before 'Hass'.

The time of fruit maturity for harvesting is late, similar to 'Hass', in that the 'Eugenin' variety reaches or exceeds the minimum harvest maturity (23% dry matter) almost at the same time as that of 'Hass'.

More particularly, the main botanical characteristics of 'Eugenin' are as follows:

*Tree growth habit*.—Spreading.
*Young shoot color*.—Reddish.
*Leaf blade anise aroma*.—Absent or weak.
*Flowering type*.—A.
*Mature fruit length*.—Short (as Edranol).
*Mature fruit diameter*.—Small (as Edranol).
*Mature fruit ratio length/diameter*.—Small (as Edranol).
*Mature fruit surface*.—Rough.
*Pedicel* (*thickness compared to peduncle at junction*).—Thicker.
*Pedicel* (*length*).—Long.
*Pedicel* (*shape*).—Cylindrical.
*Pedicel* (*nailhead*): Absent.
*Ripe fruit* (*color*).—Dark Purple or Black.
*Ripe fruit* (*thickness of skin*).—Moderately thick.
*Seed* (*shape in longitudinal section*).—Ovate.
*Color of youngest flush* (*not active*).—Pantone 376 C.
*Color of* 1 *year old branch*.—Pantone 374 C.
*Color of main branches*.—Pantone 7495 C.
*Color of lenticels*.—Pantone 361 C.

Mature Leaf:

*Upper side color*.—Pantone 363 C.
*Lower side color*.—Pantone 577 C.
*Glossiness of upper side*.—Medium.
*Prominence of veins of lower side*.—Prominent Central Vein.
*Veins*.—Asymmetric.
*Color of main trunk*.—Pantone 5825 C.

Limb:

*Shape*.—Elliptic.
*Apex shape*.—Acuminate.
*Leaf torsion in all length*.—Absent.
*Torsion of apex*.—Absent.
*Leaf border undulation*.—Very weak.

The following is a description of the 'Eugenin' variety compared with the standard avocado variety 'Hass' during the evaluation process.

TABLE 1

Trunk Perimeter of 'Hass' and 'Eugenin':

| Year | 'Hass' | 'Eugenin' |
|---|---|---|
| 2002 | 28.4 s | 25.8 s |
| 2003 | 41.5 | 40.7 |
| 2004 | 50.7 | 48.6 |
| 2005 | 56.2 s | 52.1 s |

In each row: s, indicates statistical difference (T-Student, $P < 0.05$).

TABLE 2

Fruit Production per Tree (Kg/Tree)

| Year | 'Hass' | 'Eugenin' |
|---|---|---|
| 2002 | 15.8 | 18.3 |
| 2003 | 22.3 | 30.2 |
| 2004 | 88.7 | 86.4 |
| 2005 | 19.3 | 30.7 |

TABLE 3

Mean Number of fruits per Tree:

| Year | 'Hass' | 'Eugenin' |
|---|---|---|
| 2002 | 67 | 64 |
| 2003 | 92 | 110 |
| 2004 | 396 | 330 |
| 2005 | 79 | 105 |

TABLE 4

| Average fruit Weight (g) | | |
|---|---|---|
| Year | 'Hass' | 'Eugenin' |
| 2002 | 236.4 s | 286.4 s |
| 2003 | 241.2 s | 273.1 s |
| 2004 | 223.9 s | 261.7 s |
| 2005 | 243.6 s | 291.3 s |

In each row: s, indicates statistical difference (T-Student, $P < 0.05$).

TABLE 5

| Fruit length (DP), fruit equatorial diameter (DE) and their relation (DP/DE) for each cultivar's fruit: | | | |
|---|---|---|---|
| Cultivar | Polar Diameter (DP), mm | Equatorial Diameter (DE), mm | DP/DE Relation |
| 'HASS' | 96.9 s | 69.5 s | 1.40 s |
| 'EUGENIN' | 104.4 s | 71.8 s | 1.45 s |

In each column: s, indicates statistical difference (T-Student, $P < 0.05$).

TABLE 6

| Results of fruit Characteristics on size 50 fruits. | | |
|---|---|---|
| Parameter | 'HASS' | 'EUGENIN' |
| Seed weight (g) | 20.3 b | 28.9 a |
| Pulp Weight (g) | 215.2 b | 210.5 a |
| % seed weight/fruit weight | 8.6 b | 12.1 a |
| Stem Insertion Angle * | 1 a | 1 a |
| Skin Color ** | 2 a | 2 a |

$p < 0.05$ Test de Student;

* Stem Insertion Angle: 1 = 70°-90, 2 = 50°-70°, 3 = <50°.

** Color: 1 = Yellow Green; 1 ,5 = Light Green; 2 = Green; 2,5 = Dark Green 3 = Black/Green; 4 = Black

TABLE 7

| Dates in which cultivar reached harvest maturity (23% Dry Matter). | | |
|---|---|---|
| Year | 'HASS' | 'EUGENIN' |
| 2002 | August 7th | July 31st |
| 2003 | August 14th | August 21st |
| 2004 | August 23rd | August 23rd |
| 2005 | August 12th | August 12th |

What is claimed is:

1. A new and distinct variety of avocado tree, substantially as illustrated and described herein.

* * * * *